United States Patent [19]

Mathur et al.

[11] Patent Number: 5,164,516
[45] Date of Patent: Nov. 17, 1992

[54] PURIFICATION OF CYCLIC KETENE ACETALS

[75] Inventors: Saubhagya C. Mathur; Jeffrey J. Vanderbilt, both of Longview, Tex.

[73] Assignee: Eastman Kodak Company, Rochester, N.Y.

[21] Appl. No.: 654,993

[22] Filed: Feb. 14, 1991

[51] Int. Cl.$^5$ .................. C07D 321/02; C07D 317/12
[52] U.S. Cl. .................................... 549/347; 549/369; 549/430
[58] Field of Search ........................ 549/369, 430, 347

[56] References Cited

U.S. PATENT DOCUMENTS

| | | | |
|---|---|---|---|
| 3,431,281 | 3/1969 | Sawaya | 549/430 |
| 4,323,502 | 4/1982 | Mück et al. | 549/430 |
| 4,340,542 | 7/1982 | Bär et al. | 549/430 |
| 4,423,238 | 12/1983 | Fenton | 549/369 |
| 4,513,144 | 4/1985 | Fenton | 549/369 |

FOREIGN PATENT DOCUMENTS 095182 5/1983 European Pat. Off. .
3-024071 2/1991 Japan .

OTHER PUBLICATIONS

Bailey et al, *Makromol. Chem., Macromol. Symp.*, vol. 6, 81-100 (1986).
McElvain, S. M. and Curry, J. M.; *Journal American Chemical Society*, vol. 70, 3781-3786 (1948).
Taskinen and Pentikainen, *Tetrahedron*, vol. 34, 2365-2370 (1978).
Bailey et al, *J. Polymer Science* (Poly. Chem. Ed. vol. 20, 3021-3030 (1982).
Fukuda et al, *Tetrahedron Letters*, vol. 27, No. 14, 1587-1590 (1986).

*Primary Examiner*—C. Warren Ivy
*Assistant Examiner*—A. A. Owens
*Attorney, Agent, or Firm*—Mark A. Montgomery; William P. Heath, Jr.

[57] ABSTRACT

An improved process for the purification of cyclic ketene acetals such as 2-methylene-1,3-dioxepane is provided. This process entails the purification of the cyclic ketene acetal by distillation in the presence of a solvent and an amine.

15 Claims, No Drawings

PURIFICATION OF CYCLIC KETENE ACETALS

FIELD OF THE INVENTION

The present invention relates to a process for preparing pure cyclic ketene acetals. More particularly, the present invention relates to a process for recovering and purifying cyclic ketene acetals in stable form, such as 2-methylene-1,3-dioxepane.

BACKGROUND OF THE INVENTION

Synthetic polymeric materials are widely used in a variety of applications. The environmental degradability of these polymeric materials has recently become important, primarily due to the concerns of limited landfill space and accumulation of liter. Synthetic polymers are in general not biodegradable. The carbon to carbon bonds in the backbone of most synthetic addition polymers are not very susceptible to biological cleavage and this makes these polymers generally quite resistant to biodegradation.

One possible method of solving this problem would be to blend degradable materials, such as starch, with synthetic polymers so that the structure, such as a film, is broken down and looses its structural integrity by the action of living organisms or light. However, when this happens, the actual synthetic polymer itself is not degraded but is simply in the environment in a particulate form. Thus, synthetic polymers that are themselves biodegradable and would disappear from the environment are very desirable.

Low melting, low molecular weight polyesters are known to be biodegradable. Synthetic addition polymers with an easily hydrolyzable group, such as an ester group, in the polymer chain are also known to be biodegradable. Copolymers of cyclic ketene acetals such as 2-methylene-1,3-dioxepane and ethylene are known see Bailey et. al., *Makromol. Chem., Macromol Symp.*, Vol. 6, 81-100 (1986). These copolymers are prepared with ethylene in the presence of a peroxide initiator resulting in a copolymer containing ester groups in the backbone. Processes for producing these cyclic ketene acetals are known, however, these processes have low yield, low conversion, are time consuming and/or are expensive and in some instances produce unstable cyclic ketene acetals that decompose or polymerize spontaneously.

Cyclic ketene acetals are unstable compounds and in general lead to spontaneous polymerization. The tendency to polymerize increases as the purity of the product increases. Processes for purifying these cyclic ketene acetals are known, however, these processes do not prevent spontaneous polymerization and do not produce relatively pure cyclic ketene acetals and/or are time consuming and expensive.

McElavin, S. M. and Curry, J. M.; *Journal American Chemical Society*, Vol. 70, 3781-3786 (1948) disclose the synthesis of 2-methylene-1,3-dioxolanes and 1,3-dioxanes by dehydrohalogenation of the corresponding halogenated cyclic acetals using potassium t-butoxide in t-butyl alcohol. The cyclic ketene acetals were obtained pure only with difficulty because the purer the acetal the more rapidly it polymerized.

U.S. Pat. No. 3,431,281 discloses 2-methylene-1,3-dioxolane which does not immediately polymerize. This compound is prepared by mixing 2-chloromethyl-1,3-dioxolane with a solution of liquid ammonia and a alkali metal such as sodium or potassium. It was disclosed that the monomer could be stored for at least 10 days.

Taskinen and Pentikainen, *Tetrahedron*, Vol. 34, 2365-2370 (1978) disclose the preparation Of 2-methylene-1,3-dioxepane and other cyclic ketene acetals by dehydrohalogenation of the chlorine derivatives with solid potassium t-butoxide. 2-methylene-1,3-dioxolane was not isolated as a pure compound (it polymerized immediately) but as a mixture with the other reaction product t-butanol. In many cases the ketene acetal was collected as a mixture with t-butanol. The alcohol could be removed from the mixture by azeotropic distillation with hexane, after which the pure ketene acetal could be collected unless it was too readily polymerizable to allow isolation in pure state.

Bailey et. al., *J. Polymer Science* (*Poly. Chem. Ed. Vol.* 20, 3021-3030(1982) disclose synthesis of 2-methylene-1,3-dioxepane by dehydrohalogenation of the corresponding chlorine derivative using potassium t-butoxide in t-butyl alcohol. Ether was added and the precipitate was removed by filtration. Solvents were removed by distillation and the crude product was vacuum distilled to give a product containing a trace of t-butanol. Further purification by distillation from metallic sodium produced 72 percent yield of 2-methylene-1,3-dioxepane, disclosed as being surprisingly stable. An alternative method for synthesizing 2-methylene-1,3-dioxepane using potassium hydroxide in I hexadecene with 2-chloromethyl-1,3-dioxepane was also disclosed. After 12 hours at 130° C., the product was distilled from the mixture under partial vacuum to give a liquid, which was further purified by distillation over metallic sodium to give a yield of 66 percent.

EP 095,182 discloses the synthesis of several cyclic ketene acetals including 2-methylene-1,3-dioxepane using dehydrohalogenation of the halogen derivatives using potassium t-butoxide in t-butyl alcohol. The reaction took 8 hours at 100° C. After 8 hours the mixture was extracted with ether. After removing the solvent, the residue was distilled under reduced pressure to obtain 72 percent yield of the product 2-methylene-1,3-dioxepane.

Fukuda et. al., *Tetrahedron Letters*, Vol. 27, No. 14, 1587-1590(1986) disclose the synthesis of cyclic ketene acetals using dehydrohalogenation of the chloro derivative by potassium t-butoxide in t-butyl alcohol. The isolation and purification steps were not reported.

Although the preparation and isolation of cyclic ketene acetals such as 2-methylene-1,3-dioxepane are known the above processes either produce unstable forms, are very slow and expensive, or have poor conversion and selectivity. It would, therefore, be desirable to be able to produce pure cyclic ketene acetals for the preparation of biodegradable synthetic polymers that are efficient and effective.

SUMMARY OF THE INVENTION

The process for the purification of cyclic ketene acetals from a crude product mixture containing an organic phase and an inorganic phase according to the present invention comprises: (a) separating the organic phase containing dissolved cyclic ketene acetal in solvent from the inorganic phase; and (b) distilling the organic phase in the substantial absence of oxygen in the presence of an amine having a boiling point below the boiling point of the cyclic ketene acetal, thereby recovering purified cyclic ketene acetal.

DETAILED DESCRIPTION OF THE INVENTION

The process for the purification of cyclic ketene acetals from a crude product mixture containing an organic phase and an inorganic phase according to the present invention preferably comprises separating the organic phase containing dissolved cyclic ketene acetal in solvent from the inorganic phase; adding an amine having a boiling point below the boiling point of the cyclic ketene acetal to the organic phase; and distilling the organic phase under reduced pressure or inert atmosphere thereby recovering purified cyclic ketene acetal.

The present invention involves an improved method for isolating and purifying cyclic ketene acetals, such as 2-methylene-1,3-dioxepane by separating the organic phase containing dissolved cyclic ketene acetal in solvent followed by distilling in the presence of an amine and the substantial absence of oxygen. This process results in the isolation of pure cyclic ketene acetal without decomposition or polymerization. This process is also a much simpler process and does not require the additional distillation of the product over metallic sodium.

The cyclic ketene acetals are preferably prepared in a crude form by dehydrochlorination of the halogenated cyclic ketene acetal in the presence of a hydroxide compound in a non reactive alcohol (non-reactive towards the cyclic ketene acetal). This preferred method of preparation is disclosed in the application entitled "Synthesis of Cyclic Ketene Acetals", application Ser. No. 07/654,994 filed Feb. 14, 1991 by Saubhagya C. Mathur one of the inventors of the present invention. The disclosure of which is incorporated herein by reference.

This preferred method of producing cyclic ketene acetals comprises reacting at an elevated temperature a halogenated cyclic ketene acetal with a hydroxide compound selected from alkali metal hydroxides, alkaline earth metal hydroxides, and mixtures thereof in a non reactive alcohol capable of dissolving the hydroxide compound at the elevated temperature thereby producing a cyclic ketene acetal, wherein the concentration of the hydroxide compound in the alcohol solution is between about 20 and 80 weight percent based on the total of hydroxide compound and alcohol. This preferred method of producing cyclic ketene acetals more preferably comprises reacting at an elevated temperature 2-chloromethyl-1,3-dioxepane with a hydroxy compound selected from alkali metal hydroxides, alkaline earth metal hydroxides and mixtures thereof in 2-butanol wherein the concentration of hydroxide compound in 2-butanol is between about 20 and 80 weight percent based on the total of hydroxide compound in 2-butanol.

The cyclic ketene acetals that are purified according to the process of the present invention are preferably represented by the general formula:

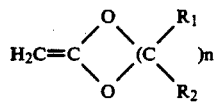

wherein $n=2$ to 4, and $R_1$ and $R_2$ each independently represent hydrogen or alkyl groups having 1 to 8 carbon atoms, or aryl groups. The preferred cyclic ketene acetals are selected from the group consisting of 2-methylene-5-dimethyl-1,3-dioxepane; 2-methylene 5-dimethyl1,3-dioxolane; 2-methylene-5-dimethyl-1,3-dioxane; 4-n-hexyl 2-methylene-1,3-dioxolane; 4-n-octyl-2-methylene-1,3-dioxolane; 4-n-decyl-2-methylene-1,3-dioxolane; 2-phenyl-4-methylene-1,3-dioxolane; cis-and trans-4,7-dimethyl-2-methylene-1,3-dioxepane; 5,6-benzo-2-methylene-1,3-dioxepane; 2-methylene-4-phenyl-1,3-dioxolane and 2-methylene 1,3-dioxepane with 2-methylene-1,3-dioxepane being most preferred. The preferred halogenated cyclic ketene acetals used to prepare the cyclic ketene acetals are the corresponding chloromethyl compounds such as 2-chloromethyl-1,3-dioxepane.

The halogenated cyclic ketene acetal is preferably prepared by the reaction of the halo acetaldehyde dialkyl acetal with a diol having from 2 to 4 carbon atoms. The preferred halogenated cyclic ketene acetal is 2 chloromethyl 1,3-dioxepane prepared from the reaction of chloroacetaldehyde dimethyl acetal with 1,4-butanediol in the presence of an acid catalyst.

The acid catalyst used in the preparation of the halogenated cyclic ketene acetal can include any acidic compound such as hydrochloric acid, sulfuric acid, para toluene sulphonic acid. The acid is preferably in an acidic ion exchange resin. Examples of suitable acidic ion exchange resins include AMBERLYST 15 and DOWEX 50 produced by Rohm & Haas and Dow Chemical respectively and available from Aldrich Chemicals. The preferred catalyst is an ion exchange resin in fine powder form having a particle size between about 50 and 100 dry mesh.

Once the cyclic ketene acetal is prepared by whatever process it is purified by removing the organic phase and fractionally distilling the organic phase under reduced pressure in the presence of an amine.

This process more particularly comprises:
(a) separating the organic phase containing dissolved cyclic ketene acetal in solvent from the inorganic phase; and
(b) adding an amine having a boiling point below the boiling point of the cyclic ketene acetal; and
(c) distilling the mixture in the substantial absence of oxygen, such as under reduced pressure or inert atmosphere, thereby recovering purified cyclic ketene acetal.

Once the organic phase is separated from the inorganic phase, it is preferred that the inorganic phase be dissolved in water preferably distilled water. It is preferred however that this water be added to the inorganic phase prior to phase separation to dissolve all the salt and base present. The amount of distilled water added should be enough to dissolve all the salt formed and the excess base present in the reaction pot when the cyclic ketene acetal is prepared according to the preferred process of dehydrohalogenation. The amount of distilled water can range from about 100 to 300 per 100 parts by weight of base used in the reaction. More preferably between about 150 to 250 parts per hundred parts with about 200 to 225 parts per hundred parts by weight base being most preferred.

The solvent present in the organic phase or the solvent used to take up the organic phase preferably is or contains a solvent that has a lower boiling point than the cyclic ketene acetal. This solvent is preferably selected from alkenes having 6 to 10 carbon atoms, cyclic aliphatic hydrocarbons having 6 to 8 carbon atoms, and aromatic aliphatic hydrocarbons. The lower boiling solvent is more preferably selected from toluene and xylene with toluene being most preferred. Prior to the phase separation it is preferred that an additional amount of organic solvent be added to the organic phase. This solvent can be the same or different from the solvent present in the organic phase after preparation of the cyclic ketene acetal.

When the solvent used to take up the organic phase contains a solvent that has a lower boiling point than the cyclic ketene acetal it is preferred that an additional high boiling solvent compound be added prior to distillation. The cyclic ketene acetal is also soluble in this high boiling compound. This high boiling compound is preferably selected from alkanes having 10 to 14 carbon atoms and alkenes having 14 to 16 carbon atoms with the most preferred higher boiling compound being 1 hexadecene. It is preferred that the amount of high boiling compound present in the mixture during distillation be between about 5 and 50 parts per hundred parts by weight of the crude reaction mixture. More preferably between about 10 and 30 parts per hundred parts with about 15 and 20 parts per hundred parts by weight of the crude reaction mixture being most preferred.

The amount of total solvent present during the distillation of the mixture according to the present invention is preferably between about 50 to 300 parts per hundred parts by weight of the cyclic ketene acetal with about 100 to 250 parts per hundred parts being more preferred and about 125 to about 175 parts per hundred parts by weight of the cyclic ketene acetal being most preferred.

The solvent(s) used in the process of the present invention for taking up the organic phase must have adequate solubility for the cyclic ketene acetal; however, these solvents should not react with the cyclic ketene acetal and the lower boiling solvent must easily be separable by fractional distillation.

The amine added to the mixture prior to distillation prevents the acid catalyzed reaction with the cyclic ketene acetal. The amine is preferably added to the organic phase after phase separation. The amount of amine preferably ranges from about 2 parts to about 20 parts per hundred parts by weight of the crude reaction mixture. With about 5 to 15 parts per hundred parts being more preferred and about 8 to 12 parts per hundred parts by weight of the crude reaction mixture being most preferred.

The amine used in the distillation in the process of the present invention preferably has a boiling point lower than that of the cyclic ketene acetal compound but should not be so volatile that it evaporates rapidly under ambient conditions. The amine preferably has a boiling point ranging between about 50° to about 120° C. more preferably between about 55° to 100° C. with about 85° to 95° C. most preferred. The amine used in the distillation step of the present invention is preferably selected from diethylene amine, di-ethyl propylamine, n-butyl amine, isobutyl amine, t-butyl amine, 2-butyl amine, and triethylamine with triethylamine being most preferred.

The distillation step of the present invention involves fractional distillation of the crude product under reduced pressure or inert atmosphere. The distillation pot containing the crude mixture and a few boiling chips is preferably connected to an Oldershaw column. The pressure is then reduced by a vacuum pump. The preferred pressure is between about 30 and 80 mm of mercury, with about 45 mm to 75 mm being more preferred and about 65 mm being most preferred. Once the pure component starts to collect the percent take off varies from about 5 to 30% with about 5% being most preferred.

The following examples are set forth to illustrate the present invention but are not intended to limit the reasonable scope thereof.

EXAMPLES

Example 1-Preparation of 2-chloromethyl-1,3-dioxepane 500 gms of chloroacetaldehyde dimethyl acetal (Aldrich catalog no C1940-6), 360 gms of 1,4-butanediol (Aldrich catalog no. 88,480 7) and 10 gms of Dowex 50 resin (Aldrich catalog No. 21,749-2) were placed in a 1000 ml, 3-neck round bottom flask equipped with a thermometer, a mechanical stirrer, a 8 inch Pen State column, and a distillation head. The mixture was heated to 115° C. under nitrogen blanket and methanol was removed continuously and the amount collected was measured by weigh up. The reaction was monitored by analyzing samples taken from the distillate in a Gas Chromatograph with a dimethyl silicon column in the temperature range of 50° C. to 250° C. The reaction was stopped when the stoichiometric amount of methanol was collected. The crude reaction mixture was filtered to remove the ion exchange resin. The product 2-chloromethyl 1,3-dioxepane was isolated from the crude mixture by fractional distillation in an Oldershaw column under partial vacuum. The fraction boiling at 105° C. at 55 mm of Hg was collected. The structure was confirmed by elemental analysis and proton NMR. Elemental analysis: C-47.2 percent (48 percent calculated), H=7.58 percent (7.33 percent calculated), 0=22.64 percent (21.34 percent calculated), Cl=22.57 percent (23.3 percent calculated). Proton NMR:1.71-1.34 ppm multiplet (—OCH$_2$CH$_2$CH$_2$C-H$_2$O—), 3.46-3.48 ppm doublet (—CH$_2$Cl), 3.66-2.96 ppm 2 sets of triplets (—OCH$_2$; 2 sets, 4 protons), 4.83-4.87 ppm triplet (ClCH$_2$CH(O)$_2$).

EXAMPLE 2

Preparation of 2-methylene-1,3-dioxepane Using Potassium Hydroxide in 2-Butanol 62.5 grams of KOH and 47 gms of 2-butanol were added to a 4 neck 1 liter round bottom flask equipped with a thermometer, a reflux condenser, a pressure-relief addition funnel, and a mechanical stirrer. The mixture was heated to 125° C. until all the KOH pellets were dissolved. 37.5 grams of 2-chloromethyl-1,3-dioxepane synthesized using the method described in Example 1 was added drop wise using the addition funnel. After complete addition, the reaction was allowed to occur for 2 hours. Heat was cut off and 100 gms of distilled water and 50 gms of toluene were added to the reaction mixture. The organic phase was separated in a separatory funnel. A gas chromatograph on a sample taken from the reaction mixture indicated complete conversion of 2-chloromethyl-1,3-dioxepane and a 72% crude yield for 2-methylene-1,3-dioxepane was observed.

EXAMPLE 3

Example 2 was repeated with 270 gms of KOH, 180 gms of 2-butanol and 150 gms of 2-chloromethyl-1,3-dioxepane. The organic phase was taken up in 207 gms of toluene and the inorganic phase was taken in 400 gms of distilled water. At the end of the reaction, 62.9 percent crude yield was observed.

EXAMPLE 4

Recovery of 2-methylene-1,3-dioxepane from the crude reaction mixture 619 gms of the organic phase collected from examples 2 and 3 were mixed with 100 gms of 1-hexadecene and 56 gms of Triethyl amine. The mixture was subjected to fractional distillation in an Oldershaw column under partial vacuum. The fraction boiling at 78° C. at 63 mm was collected. The overall yield was 72 percent. 47 percent of the fractions were 99+percent pure and the remaining portion contained a trace of 2-butanol. The structure of the product was confirmed from proton and C-13 NMR.

EXAMPLE 5

Comparative 270 gms of KOH and 180 gms of 2-butanol were added to a 3 neck 2 liter round bottom flask equipped with a thermometer, a reflux condenser, a pressure-relief addition funnel, and a mechanical stirrer. The mixture was heated to 125° C. until all the KOH pellets were dissolved. 150 grams of 2-chloromethyl-1,3-dioxepane synthesized using the method described in example 1 was added drop wise using the addition funnel. After complete addition, the reaction was allowed to occur for 2 hours. The organic phase from the crude reaction mixture was filtered to remove the solids. Another batch was prepared using same procedure. The liquid obtained from the two batches (458.7 grams) was subjected to fractional distillation under reduced pressure in an Oldershaw column which had been cleaned by distilling ammonia and 2-butanol through it. Several fractions boiling in the range of 35° to 58° C. at 39-40 mm of Hg were collected. Gas chromatography indicated the presence of 2-methylene-1,3-dioxepane in these fractions along with 2-butanol. No fraction containing just the desired product could be isolated.

EXAMPLE 6

Comparative

An attempt was made to distill off the cyclic ketene acetal compound directly from the reaction pot in presence of the excess base. The reaction was carried out in 4 batches according to the preparation procedure described in Example 5. At the end of the 2 hour reaction time in each case the reflux condenser was replaced by a distillation head and the liquid phase being distilled off was collected. When no more liquid came off, 1 hexadecene (277 grams) was added and distillation was continued again. The remaining liquid in the pot was removed from the solids by rotary evaporation. Gas chromatography indicated the presence of a mixture of 2-butanol and 2-methylene-1,3-dioxepane. No pure component was collected. 675 grams of the crude liquid collected was then subjected to fractional distillation under reduced pressure. No success was obtained in isolating the pure component. Fractions were collected at boiling points ranging from 30° C. to 60° C. at 27 millimeters to 130 millimeters of Hg. All the fractions contained less than 10 percent of the product as indicated by Gas chromatography. The fractions collected later indicated the presence of several high boiling components while the peak associated with the desired product disappeared.

EXAMPLE 7

Comparative 180 gms of KOH and 120 gms of ethanol were added to a 3 neck 1000 ml round bottom flask equipped with a mechanical stirrer, a reflux condenser and a thermometer. The mixture was heated and at 100° C., 90 gms of 2-chloromethyl-1,3-dioxepane was added dropwise to the reaction mixture. The reaction was allowed to occur for 1 hour. Heating was stopped and 150 ml of distilled water was added to the mixture. 162 grams of the organic phase was isolated by dissolving the inorganic phase in distilled water. The mixture was subjected to fractional distillation under reduced pressure. No pure component was isolated. A thick paste started to develop in the distillation pot indicating polymerization.

EXAMPLE 8

Comparative 180 grams of KOH and 120 gms of ethanol were added to a 3 neck 1000 ml round bottom flask equipped with a mechanical stirrer, a reflux condenser, and a thermometer. The mixture was heated and at 90° C., 99.97 grams of 2-chloromethyl-1,3-dioxepane was added dropwise to the reaction mixture. The reaction was allowed to occur for about 1 hour. GC indicated formation of the desired product along with one higher boiling component. Heating was stopped and 100 ml of distilled water was added to the mixture. 48.5 grams of organic phase was separated. The above organic phase was mixed with 188 gms of 1-hexadecene in a 1 liter round bottom distillation flask which was prewashed in caustic solution. The distillation column was first cleaned by distilling ammonium hydroxide and then ethanol through it. Fractional distillation of the crude product through the column did not yield the desired product. A solid residue started to form in the flask and the distillation process was discontinued. GC indicated absence of the product in the flask.

EXAMPLE 9

Comparative

The reaction described in example 8 was repeated. 150 ml of distilled water was added after 1 hour of reaction and the organic phase was separated. 168 gms of organic phase isolated after filtering was mixed with 121 gms of 1-hexadecene and 119 gms of KOH. GC indicated the presence of ethanol, 2-methylene-1,3-dioxepane, 1-hexadecene and 1-byproduct. The mixture was subjected to fractional distillation under reduced pressure. Ethanol was the first component to distill. But as soon as ethanol was depleted, several higher boilers formed. 2-methylene-1,3-dioxepane could not be isolated. The product had reacted in the distillation pot.

The invention has been described in detail with particular reference to the preferred embodiments thereof, however, it should be understood that variations and modifications can be made without departing from the reasonable scope thereof.

We claim:

1. A process for the purification of cyclic ketene acetals from a crude product mixture containing an organic phase and an inorganic phase comprising:

(a) separating the organic phase containing dissolved cyclic ketene acetal in solvent from the inorganic phase; and (b) distilling the organic phase in the substantial absence of oxygen in the presence of an amine having a boiling point below the boiling point of the cyclic ketene acetal, thereby recovering purified cyclic ketene acetal.

2. The process according to claim 1 wherein said cyclic ketene acetal is represented by the general formula

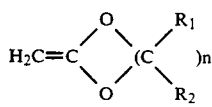

wherein n=2 to 4, and $R_1$ and $R_2$ each independently represent hydrogen, alkyl groups having 1 to 8 carbon atoms or aryl groups.

3. The process according to claim 2 wherein said cyclic ketene acetal is selected from the group consisting of: 2-methylene-5-dimethyl-1,3-dioxepane; methylene-5-dimethyl-1,3-dioxolane; 2-methylene-5-dimethyl-1,3-dioxane; 4-n-hexyl-2-methylene-1,3-dioxolane; 4-n-octyl- 2-methylene-1,3-dioxolane; 4-n-decyl-2-methylene-1,3-dioxolane; 2-phenyl-4-methylene-1,3-dioxolane; cis-and trans-4,7-dimethyl methylene-1,3-dioxepane; 5,6-benzo-2-methylene-1,3-dioxepane; 2-methylene-4-phenyl-1,3-dioxolane and 2-methylene-1,3- dioxepane.

4. The process according to claim 3 wherein said cyclic ketene acetal is 2-methylene-1,3-dioxepane.

5. The process according to claim 1 wherein the amine is added after step (a), is present during the distillation in an amount between about 2 and about 20 parts per hundred parts by weight of the crude reaction mixture, and is selected from amines having a boiling point in the range of about 50° C. to about 120° C.

6. The process according to claim 5 wherein the amine is selected from dimethyl amine, di-n-propyl amine, n-butyl amine, isobutyl amine, t-butyl amine, sec-butyl amine, and triethyl amine.

7. The process according to claim 6 wherein said amine is triethyl amine.

8. The process according to claim 1 wherein the solvent contains a high boiling compound selected from alkanes having 10 to 14 carbon atoms and alkenes having 14 to 16 carbon atoms in which the cyclic ketene acetal is soluble.

9. The process according to claim 8 wherein the higher boiling compound is 1-hexadecene present in the mixture during distillation in an amount between about 5 and about 50 parts per hundred parts by weight of the crude reaction mixture.

10. The process according to claim 8 wherein the solvent in the mixture also contains a solvent that has a lower boiling point than the cyclic ketene acetal.

11. The process according to claim 10 wherein the lower boiling solvent is added prior to phase separation and is selected from alkenes having 6 to 10 carbon atoms, cyclic aliphatic hydrocarbons having 6 to 8 carbon atoms and aromatic aliphatic hydrocarbons.

12. The process according to claim 11 wherein said lower boiling solvent is toluene.

13. The process according to claim 1 wherein an additional amount of organic solvent that is the same or different than the solvent present is added to the organic phase prior to phase separation.

14. The process according to claim 1 wherein the amount of solvent present during the distillation of the mixture is between about 50 to about 300 parts per hundred parts by weight of the cyclic ketene acetal.

15. The process according to claim 1 wherein a sufficient amount of water is added to the inorganic phase prior to phase separation to dissolve all salt and base present.

* * * * *

UNITED STATES PATENT AND TRADEMARK OFFICE
CERTIFICATE OF CORRECTION

PATENT NO.  : 5,164,516
DATED       : November 17, 1992
INVENTOR(S) : Saubhagya C. Mathur and Jeffrey J. Vanderbilt It is certified that error appears in the above-identified patent and that said Letters Patent is hereby corrected as shown below:

Claim 3:

Column 9, line 26, should read " . . . 2-methylene-5-dimethyl-1,3-dioxepane; 2-methy-" and Column 9, line 31, should read " . . . cis-and trans-4,7-dimethyl 2-methylene-1,3-dioxe-"

Claim 6:

Column 10, line 4, should read "diethyl" instead of "dimethyl"

Signed and Sealed this

Twenty-sixth Day of October, 1993

Attest:

BRUCE LEHMAN

Attesting Officer

Commissioner of Patents and Trademarks